US00PP34243P2

(12) United States Plant Patent
Zlesak

(10) Patent No.: US PP34,243 P2
(45) Date of Patent: May 17, 2022

(54) ***PHYSOCARPUS* PLANT NAMED 'ZLEMICHAEL'**

(50) Latin Name: *Physocarpus opulifolius*
Varietal Denomination: ZLEMichael

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 0 days.

(21) Appl. No.: 17/300,971

(22) Filed: Jan. 4, 2022

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 6/74; A01H 5/02
See application file for complete search history.

*Primary Examiner* — Keith O. Robinson

(57) ABSTRACT

'ZLEMichael' is a new and distinct cultivar of *Physocarpus opulifolius* plant having an upright, mounded, dense plant habit; compact overall plant size; strong branching characteristics; small-medium sized yellow-green foliage; short internode length; resistance to powdery mildew; corymbs of small blush-white flowers; pastel coral-pink follicle color in full sun for about a month after fertilization; and ability to root and grow vigorously from softwood and semi-hardwood stem cuttings.

5 Drawing Sheets

Latin name of genus and species: *Physocarpus opulifolius.*

Variety denomination: 'ZLEMichael'.

BACKGROUND OF THE INVENTION

The present invention relates to a new and distinct cultivar of *Physocarpus opulifolius* and will be referred to hereafter by its cultivar name, 'ZLEMichael'. *Physocarpus opulifolius* (commonly known as ninebark, common ninebark, Altantic ninebark, and Eastern ninebark) is a deciduous shrub grown for landscape use. The key objective within the *Physocarpus opulifolius* breeding program I initiated in St. Paul, Minn. in 2001 and now continue in River Falls, Wis. is to develop new *Physocarpus opulifolius* cultivars that are compact growing, well-branched, healthy, and possess colorful foliage. One specific goal has been to produce a cultivar with the yellow-green foliage color of *Physocarpus opulifolius* 'Dart's Gold' (not patented) and the compact, well-branched growth habit and small foliage of cultivars such as *Physocarpus opulifolius* var. *nanus* (not patented) and its descendant *Physocarpus opulifolius* 'Donna May' (disclosed in U.S. Plant Pat. No. 22,634).

'ZLEMichael' originated as a unique seedling within an $F_2$ population that was developed by open-pollination of twelve $F_1$ seedlings (growing in isolation) from the cross *Physocarpus opulifolius* 'Donna May' as the female parent and *Physocarpus opulifolius* 'Dart's Gold' as the male parent. The specific $F_1$ seedling that was the maternal parent of 'ZLEMichael' is 2013-7, a compact growing genotype with small purple foliage. Ninebark displays self-incompatibility and the seed collected from 2013-7 is expected to have arisen from crosses with its full siblings. The pollination that led to the population of seedlings from which 'ZLEMichael' was identified occurred in June 2015. The seeds of this population germinated during the winter of 2015/2016 indoors under florescent lights in St. Paul, Minn.

Seedlings were grown in containers during their first year. At the end of the first growing season, seedlings with attractive foliage color, relatively compact growth habits, and powdery mildew resistance were retained, which included 'ZLEMichael'. In 2017 softwood cuttings were taken to asexually propagate 'ZLEMichael' and the original seedling was planted in an outdoor ground bed. 'ZLEMichael' continued to be recognized as a highly desirable genotype and stem cuttings were taken each summer since 2017 to have more plants on hand for production and landscape trials in River Falls, Wis. and Cottage Grove, Minn. I have found that the characteristics of 'ZLEMichael' are stable and true to type over successive generations of vegetative propagation.

'ZLEMichael' is unique compared to other ninebark seedlings in my breeding program and all cultivars I am aware of because of its small to medium sized yellow-green foliage and compact, well-branched plant habit. For a compact growing, well-branched, yellow-green leaved ninebark with petite foliage, the foliage size is significantly larger than other similar genotypes (~25% larger). The relatively larger foliage size for a compact ninebark allows the yellow-green foliage color to be more prominent from a distance and adds to its ornamental value. 'ZLEMichael' first flowered in 2017 with blush-white flowers that are abundant and attractive against the yellow-green foliage. As follicles develop in full sun, they have a pastel coral-pink color for about a month and provide additional ornamental value. 'ZLEMichael' naturally branches on vigorous current season's growth without pruning. This leads to an abundance of stems and a dense growth habit.

SUMMARY OF THE INVENTION

The primary objective of the breeding goal was substantially achieved, along with other desirable improvements, as evidenced by the following unique combination of characteristics that are outstanding in the new variety and that distinguish it from other ninebark in my breeding program, as well as from all other cultivars of *Physocarpus opulifolius* of which I am aware:

1. Upright, mounded, dense plant habit;
2. Compact overall plant size;
3. Strong branching characteristics;
4. Small-medium sized yellow-green foliage;
5. Short internode length;
6. Resistance to powdery mildew;
7. Corymbs of small blush-white flowers;
8. Pastel coral-pink follicle color in full sun for about a month after fertilization;
9. Ability to root and grow vigorously from softwood and semi-hardwood stem cuttings.

Asexual reproduction of this new cultivar by rooting of softwood and semi-hardwood cuttings, as performed at River Falls, Wis. and Cottage Grove, Minn. shows that the foregoing and all other characteristics and distinctions come true to form and are established and transmitted through succeeding asexual propagations.

Comparison With Parents

'ZLEMichael' is a seedling in the $F_2$ generation from a cross of 'Donna May' and 'Dart's Gold'. 'ZLEMichael' has a similar overall plant size and dense, well branched plant habit of its specific $F_1$ maternal parent 2013-7 and grandparent 'Donna May', but is different from 2013-7 and 'Donna May' in that the foliage of 'ZLEMichael' is yellow-green versus purple and the leaves are larger. Compared to 'Dart's Gold', the foliage color is similar, but the plant size and leaf size of 'ZLEMichael' are smaller. The plant habit of 'ZLEMichael' is more dense and well-branched than 'Dart's Gold'.

Comparison of 'ZLEMichael' With Similar Cultivars

The *Physocarpus opulifolius* cultivar with the greatest similarity to 'ZLEMichael' is *Physocarpus opulifolius* 'ZLEYel2' (disclosed in U.S. Plant Pat. No. 31,198). Foliage color, branching habit, compact growth, and overall plant size are similar between these cultivars. Differences are that the leaves of 'ZLEMichael' are about 25% larger than 'ZLEYel2' and that the color of the developing follicles of 'ZLEMichael' are a pastel coral-pink, while developing follicles of 'ZLEYel2' are coral-pink to red.

BRIEF DESCRIPTION OF THE DRAWINGS

The accompanying colored photographs illustrate key features of 'ZLEMichael'. Photographs show the colors as true as it is reasonably possible to obtain with colored reproductions of this type. Colors in the photographs may differ slightly from the color values cited in the detailed botanical description, which accurately describe the colors of 'ZLEMichael'.

DETAILED BOTANICAL DESCRIPTION

Figure 1:
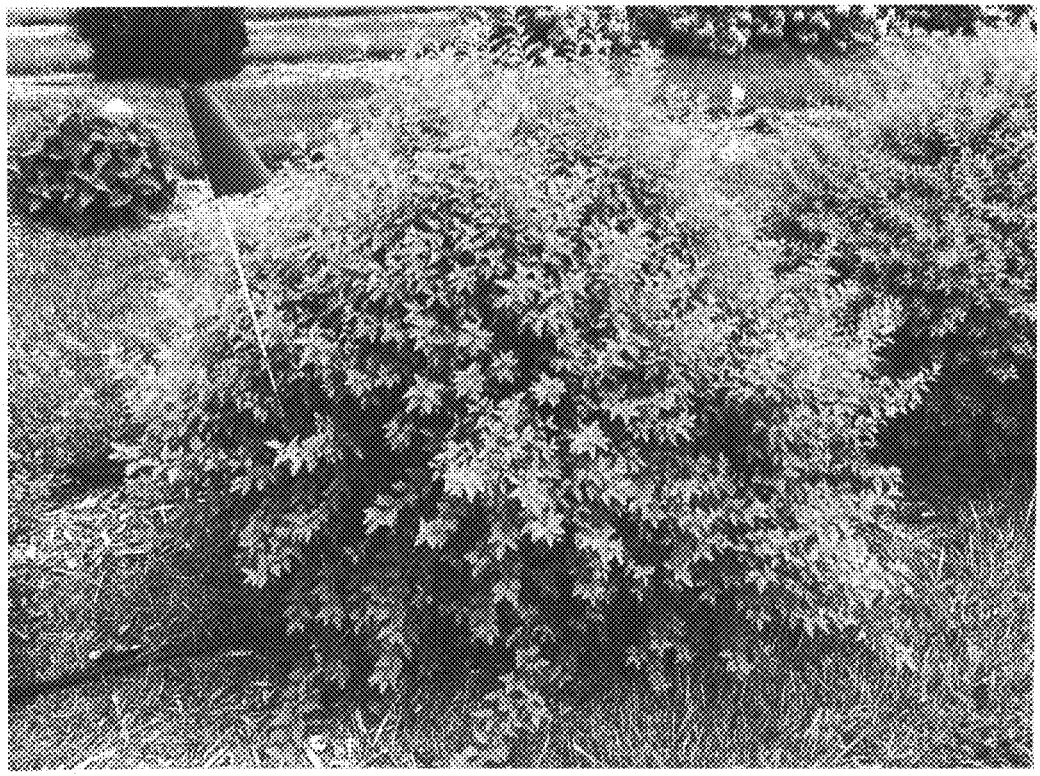
FIG. 1 illustrates a plant of 'ZLEMichael' in its fifth growing season in August 2021.
Figure 2:
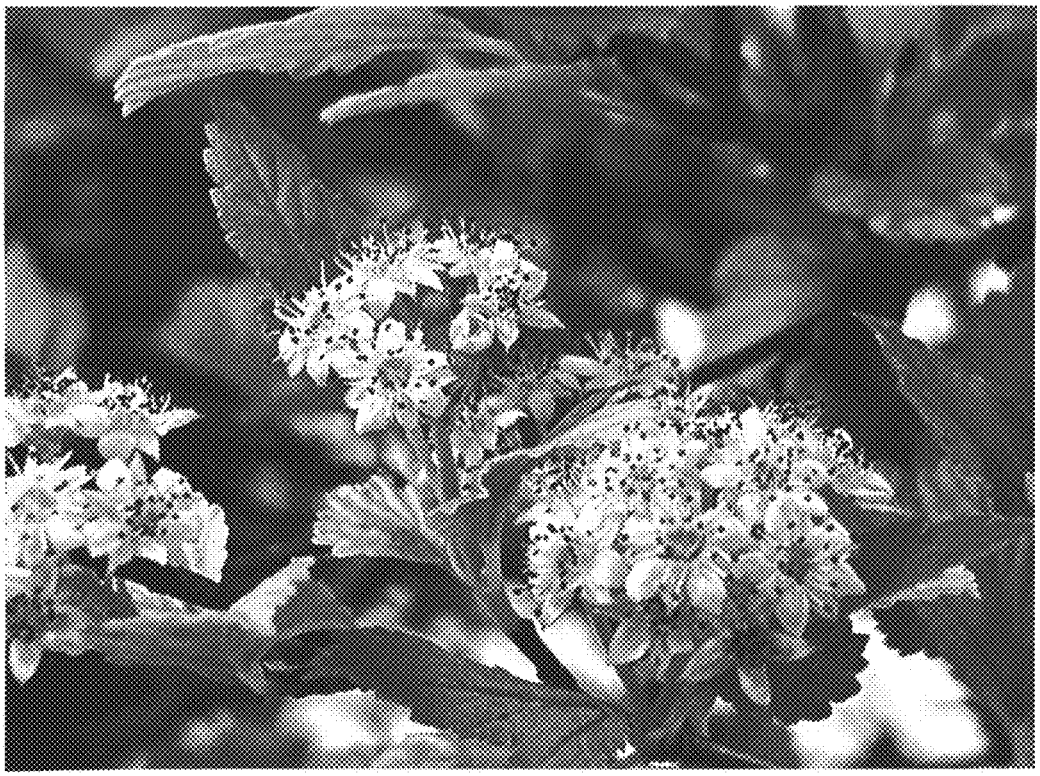
FIG. 2 illustrates corymbs of flowers of 'ZLEMichael' in mid-June 2021.
Figure 3:
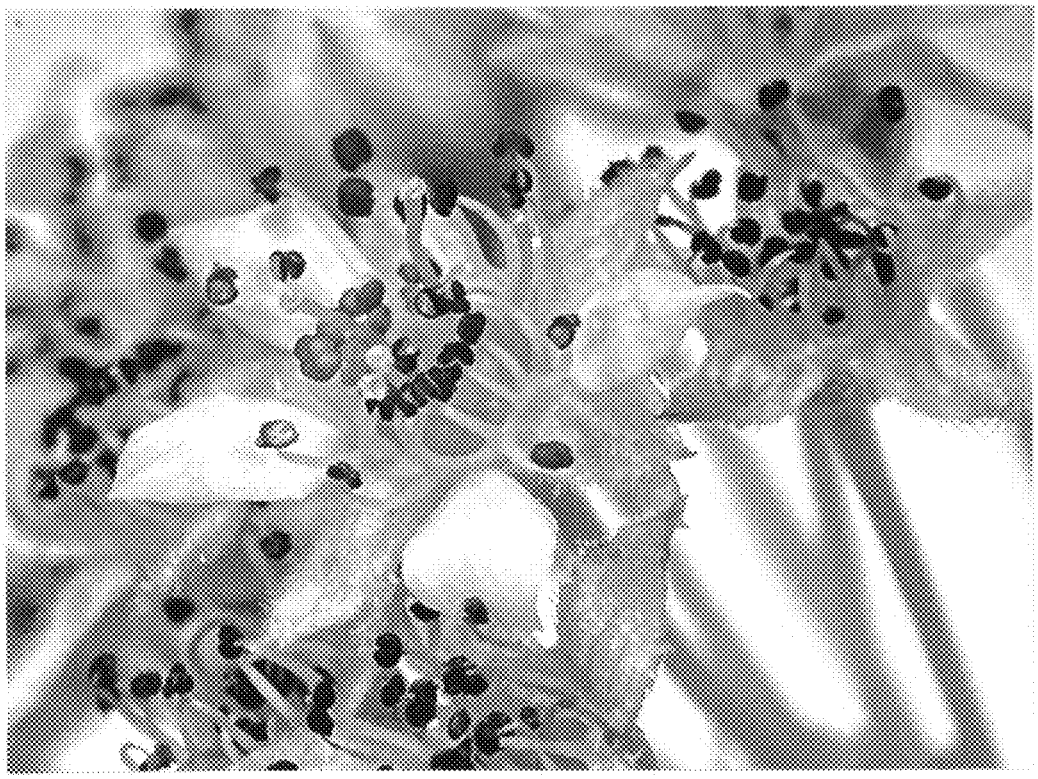
FIG. 3 illustrates a closeup of flowers of 'ZLEMichael' in mid-June 2021.
Figure 4:
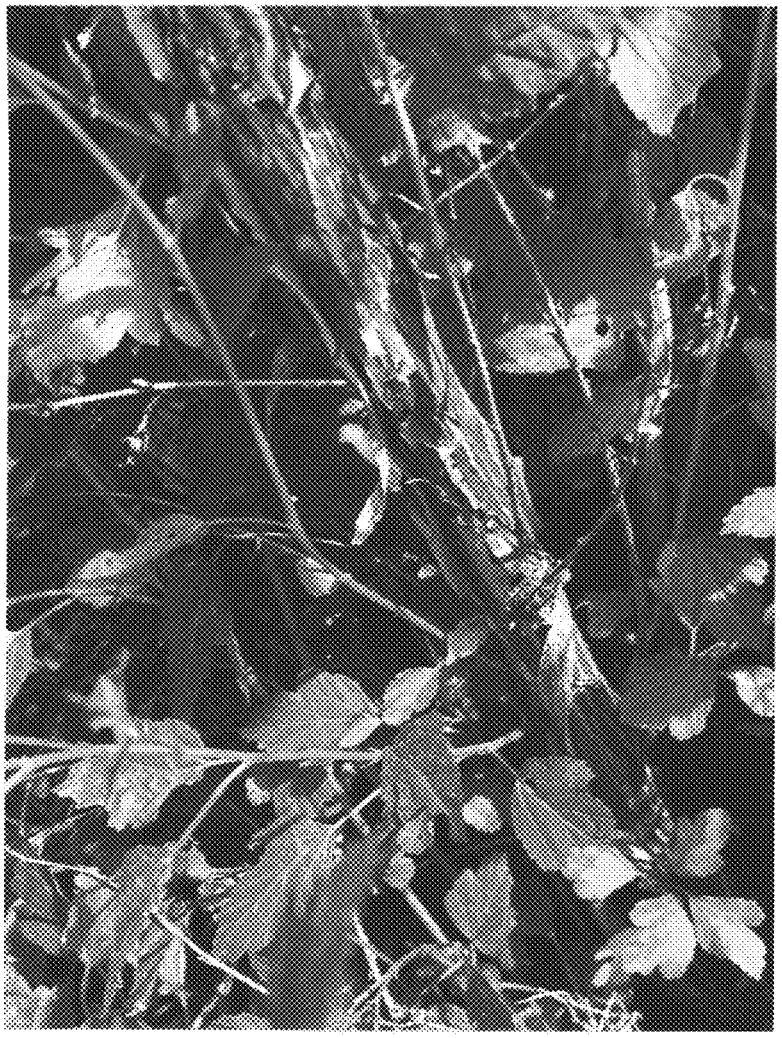
FIG. 4 illustrates the oldest stems at the base of a plant in its fifth growing season of 'ZLEMichael'.
Figure 5:
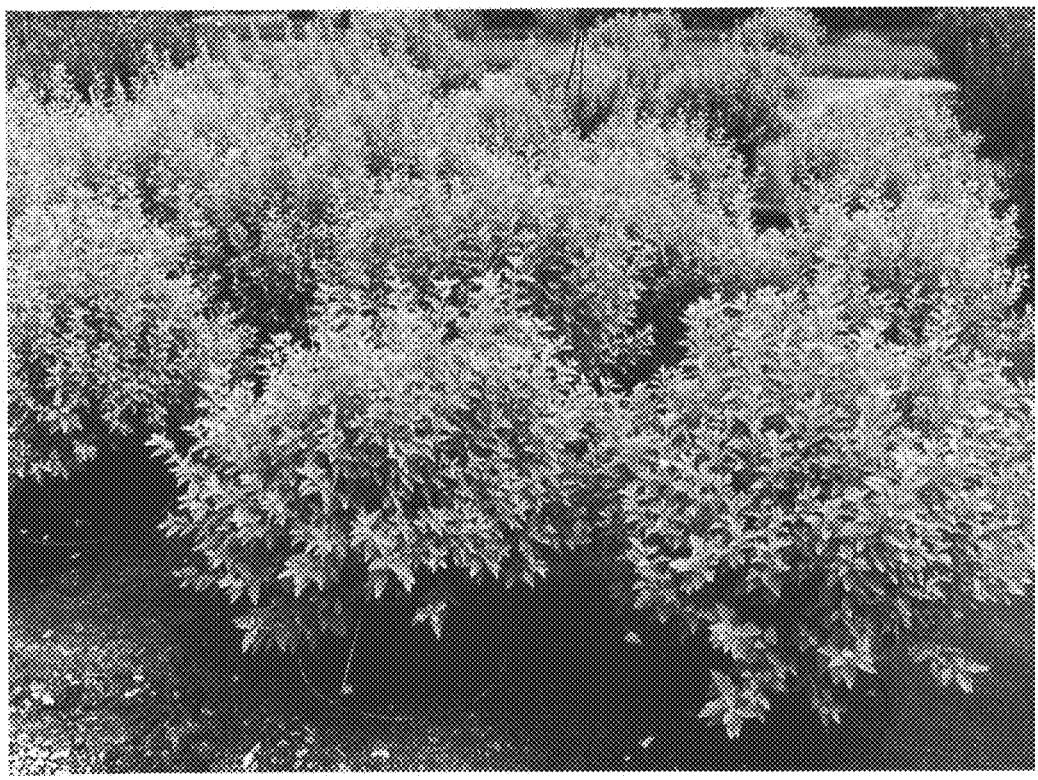
FIG. 5 illustrates two-year-old plants of 'ZLEMichael' growing in #2 nursery containers July 2021.
Figure 6:
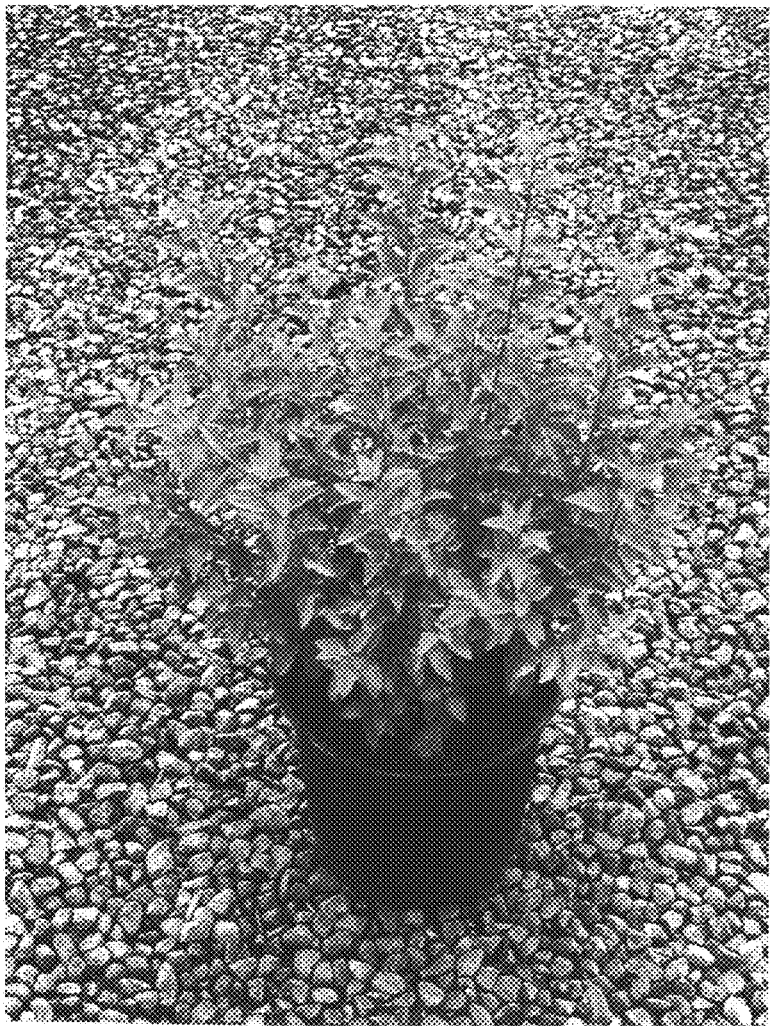
FIG. 6 illustrates a one-year-old plant of 'ZLEMichael' growing in a #2 nursery container July 2021.

The following is a detailed description of 'ZLEMichael', the new *Physocarpus opulifolius* cultivar, with color descriptions using terminology in accordance with The Royal Horticultural Society (London) Colour Chart (2015), except where ordinary dictionary significance of color is indicated. The phenotype of the new cultivar may vary with variations in environmental, climatic, and cultural conditions, as it has not been tested under all possible environmental conditions. Descriptions are based on observations of plants that are at least 4 years old growing in River Falls, Wis. and Cottage Grove, Minn. during the 2021 growing season.

Classification:

*Botanical.*—*Physocarpus opulifolius* 'ZLEMichael'.

*Common names of the species.*—Ninebark, common ninebark, Atlantic ninebark, and Eastern ninebark.

*Commercial.*—Deciduous shrub.

Parentage:

*Seed parent.*—*Physocarpus opulifolius* selection 2013-7 (non patented; cross of 'Donna May' as the maternal parent and 'Dart's Gold' as the paternal parent).

*Pollen parent.*—A *Physocarpus opulifolius* genotype that most likely is a full sibling of 2013-7. Siblings were growing in the same garden bed isolated from other ninebark cultivars and seedling populations. The specific sibling that served as the pollen parent is unknown.

General description:

*Plant habit.*—Upright, mounded, and compact.

*Plant size.*—1.0-1.3 m in overall height and width.

*Growth habit.*—Vigorous and dense with abundant branching.

*Blooming period.*—About 21 days from mid-June to early July.

*Hardiness.*—Cold hardy to at least USDA Zone 4.

*Root description.*—Fibrous and vigorous.

*Diseases and pest resistance.*—'ZLEMichael' has shown above average resistance to powdery mildew with other ninebark genotypes more heavily infected with powdery mildew growing near it. There are multiple species of fungi that cause powdery mildew on ninebark, and it is unclear which species of fungi were infecting it and the adjacent, more susceptible ninebark genotypes.

*Cultural requirements.*—'ZLEMichael' does well in full to partial sun and well-drained, moderately fertile soil.

Growth and propagation:

*Propagation.*—Softwood and semi-hardwood stem cuttings have been effective.

*Time required for root initiation and initial development.*—It takes about 3 to 4 weeks during the summer using intermittent mist in a greenhouse without supplemental lighting for cuttings to typically form visible roots.

*Time required to obtain a well-rooted cutting.*—It takes about 6 to 7 weeks to produce a well-rooted cutting in a 2-inch diameter container.

Branch description:

*Branch color.*—The color of current season stems is Yellow-Green Group N144D. Sides of current season's stems in full sun had reddish highlights closest to Red-Purple Group 58A. The most mature stems on four-year-old plants had a mixture of colors on the exfoliating bark; primarily Greyed-Orange Group 164A and Greyed-Orange Group 164C, but there were also lighter colored areas close to Greyed-Yellow Group 161D and darker colored areas close to Greyed-Orange 166A.

*Branch size.*—Branches produced during the current season of growth ranged from approximately 12-60 cm in length and 1-4 mm in width. The oldest branches on four-year-old plants were up to 1.5 cm in diameter at the base of the plant.

*Branch surface.*—Young stems: Glabrous with a slight sheen. Older stems: Exfoliating bark layers that are somewhat dull and no longer have a sheen.

*Internode length.*—1.3-2.0 cm.

*Branch habit.*—Vigorous current season's stems tend to produce new stems from axillary buds without pruning. This leads to an abundantly branched and dense plant. The angle between the new stems arising from axillary buds and the stem from which they originated is typically 20-60°.

Foliage description:

*Overall leaf size.*—Leaf length is 5.0-7.5 cm and leaf width is 2.5-4.0 cm.

*Leaf division.*—Simple.

*Leaf attachment.*—Petiolate.

*Leaf arrangement.*—Alternate.

*Leaf number.*—It varies, but a vigorous growing branch typically produces 30-60 leaves in a growing season.

*Leaf blade shape.*—Ovate in overall outline with three prominent lobes.

*Leaf blade base.*—Rounded.

*Leaf blade apex.*—Acute to cuneate.

*Leaf blade venation.*—Primary venation is palmate with three principal veins. The principal veins diverge at the juncture of the leaf blade and petiole and continue with one through the middle of each of the three lobes. Secondary venation off the three principal veins is pinnate.

*Leaf blade margin.*—The three primary lobes have secondary lobes or serrations. The margin on the three primary lobes is best described as doubly serrate. The serrations extend out from the edge of the main leaf blade about 1.0-1.5 mm and there is typically between 3-4 mm between the tips of primary serrations and 1-2 mm between the tips of secondary serrations.

*Leaf blade surface.*—Glabrous on upper and lower surfaces.

*Leaf blade size.*—The leaf blade is approximately 3.75-5.25 cm long and 2.5-4.0 cm wide.

*Leaf blade color.*—Young emerging leaf blades are Yellow-Green Group 150A on the upper and lower surfaces. Young expanded leaf blades are closest to Yellow-Green Group 145A on the upper surface and Yellow-Green Group 145B on the lower surface. Mature leaves are Green Group 137C on the upper surface and Yellow-Green Group 146B on the lower surface. Where the sun especially hits the upper surface of the leaves, the color can be Yellow-Green Group N144A.

*Petiole size.*—About 1.0-2.25 cm in length and about 1 mm in width.

*Petiole shape.*—Sulcate. The petiole is generally round except for a longitudinal furrow running the length of the upper surface.

*Petiole color.*—Yellow-Green Group 146C.

*Petiole texture.*—Glabrous.

*Stipule number.*—There are two stipules at each node with one on each side of the leaf petiole.

*Stipule size.*—2-3 mm long and 1.25 mm wide.

*Stipule shape.*—Generally lanceolate.

*Stipule color.*—Yellow-Green Group 146C on the upper and lower surfaces.

Flower description:

*Inflorescence type.*—A corymb with 17-25 rotate flowers arranged in a hemisphere.

*Inflorescence size.*—Typically 1.5-2.0 cm in height and width.

*Inflorescence lastingness.*—The corymb has open flowers typically for up to 21 days with each individual flower open for approximately 3 days.

*Flower bud shape.*—Elliptic to oval.

*Flower bud size and proportions.*—2.5-3.0 mm in length and 2.0 mm in width. The receptacle of the bud accounts for about half of the proximal end and the calyx accounts for about half of the distal end of an unopened flower bud.

*Flower bud color.*—The overall color of exposed petal undersides as the sepals open can best be described as White Group N155B. The sepals are Yellow-Green Group 146C and the receptacle color is Yellow-Green Group 153C.

*Flower size when fully open.*—4.5-5.5 mm in diameter and 4.0 mm in depth (not including pedicel).

*Flower symmetry.*—Actinomorphic.

*Flower fragrance.*—Slight and sweet.

*Petal number.*—5.

*Petal size.*—2.0-2.5 mm in length and width.

*Petal shape.*—Elliptic to obovate.

*Petal color.*—Expanding petals are White Group 155C on the upper and lower surfaces.

*Sepal number.*—5.

*Sepal size.*—Length is 2.0-3.0 mm and width is 1.0-1.5 mm.

*Sepal shape.*—Deltoid.

*Sepal color.*—Yellow-Green Group N144D on top and Yellow-Green Group 146C on bottom.

*Sepal texture.*—Hoary on both surfaces.

*Pedicel size.*—The length ranges from about 1.25 cm for the flowers coming from the proximal or lower end of the corymb to about 0.5 cm for the flowers nearest the terminal or center of the corymb. Pedicels are round in cross section and about 0.75-1.0 mm in diameter.

*Pedicel color.*—Yellow-Green Group 146D.

*Pedicel and receptacle texture.*—Glabrous.

*Subtending bract size.*—There is a subtending bract where each pedicel meets the peduncle of the corymb. The subtending bract is 1.0-3.0 mm long and 1 mm wide below where the pedicels attach at the proximal end of the corymb to 1.0-2.0 mm long and 0.75-1.0 mm wide under the more distal pedicels at the terminal or top of the corymb.

*Subtending bract shape.*—Elliptic to obovate with 5-8 very small and irregularly spaced serrations.

*Subtending bract color.*—Yellow-Green Group 146D.

Gynoecium:

*Pistil number per flower.*—Typically there are 4, but sometimes 3.

*Stigma shape.*—Globular.

*Stigma size.*—0.25 mm in height and width.

*Stigma color.*—Yellow Green Group 144D.

*Style shape.*—Linear.

*Style size.*—About 3 mm long and 0.2 mm wide.

*Style color.*—White Group 155C.

*Ovary shape.*—Elliptic.

*Ovary size.*—About 0.5 mm in length and 0.3 mm in width.

*Ovary color.*—Yellow Green Group 146D with red highlights that are Red-Purple Group 61A.

Androecium:

*Stamen number per flower.*—Approximately 25.

*Anther shape.*—Elliptic to round.

*Anther size.*—0.5 mm in height and width.

*Anther color.*—Purple Group N77B upon flowers opening and darkening to Purple Group N77A after dehiscence.

*Pollen color.*—White Group 155C.

*Pollen abundance.*—Moderate.

*Filament shape.*—Linear.

*Filament size.*—1.0-3.0 mm long and 0.1-0.2 mm wide.

*Filament color.*—White Group 155C.

Fruit and seeds:

*Fruit.*—There are typically three or four firm-walled follicles that form per flower. Follicles can split along both sides of the seam, but split more readily along the inner or adaxial seam. Follicles are elongated and generally ovate in shape with acuminate tips. They are up to 6.0 mm long and approximately 2.0 mm wide at their widest point. After fertilization and expansion of successfully developing fruit, the follicle surface has a pastel coral pink color in bright light close to Orange-Red Group 35B. Follicle color tends to be green when out of direct sunlight and near Yellow-Green Group 145C. As the follicles continue to mature the coral-pink coloration dissipates. When mature and before turning brown the color is Greyed-Yellow Group 161A. The final color when follicles open and release seeds is Greyed-Orange Group 165A.

*Seeds per follicle.*—There are typically 1-2 seeds per follicle.

*Seed shape.*—Ovate.

*Seed size.*—Up to about 1.5 mm long and 1.25 mm wide.

*Seed color.*—Mature seed color as follicles open and seeds are exposed and dehisce is closest to Greyed-Orange Group 164B.

Winter hardiness: Acclimated plants of 'ZLEMichael' have displayed strong stem survival (complete survival to minor tip dieback) in United States Department of Agriculture cold hardiness zone 4 without insulation.

I claim:

1. A new and distinct cultivar of *Physocarpus opulifolius* plant named 'ZLEMichael', substantially as herein shown and described, characterized particularly by its upright, mounded, dense plant habit; compact overall plant size; strong branching characteristics; small-medium sized yellow-green foliage; short internode length; resistance to powdery mildew; corymbs of small blush-white flowers; pastel coral-pink follicle color in full sun for about a month after fertilization; and ability to root and grow vigorously from softwood and semi-hardwood stem cuttings.

* * * * *